United States Patent
Biedermann et al.

(10) Patent No.: US 8,562,652 B2
(45) Date of Patent: Oct. 22, 2013

(54) DYNAMIC ANCHORING DEVICE AND DYNAMIC STABILIZATION DEVICE FOR VERTEBRAE

(75) Inventors: Lutz Biedermann, Villingen (DE); Jürgen Harms, Karlsruhe (DE); Helmar Rapp, Deißlingen (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 2038 days.

(21) Appl. No.: 10/841,862

(22) Filed: May 6, 2004

(65) Prior Publication Data

US 2004/0225289 A1 Nov. 11, 2004

Related U.S. Application Data

(60) Provisional application No. 60/469,086, filed on May 7, 2003.

(30) Foreign Application Priority Data

May 7, 2003 (DE) .................................. 103 20 417
Feb. 27, 2004 (WO) ................. PCT/EP2004/001978

(51) Int. Cl.
*A61B 17/70* (2006.01)

(52) U.S. Cl.
USPC .......................................................... 606/266

(58) Field of Classification Search
USPC ................................. 606/264–279, 301–320
See application file for complete search history.

(56) References Cited

U.S. PATENT DOCUMENTS

| 2,197,889 | A | | 4/1940 | Katcher |
| 2,544,583 | A | | 3/1951 | Booth |
| 2,576,830 | A | | 11/1951 | Flumerfelt |
| 2,838,330 | A | | 6/1958 | Fidler |
| 2,855,232 | A | | 10/1958 | Kozak |
| 5,176,680 | A | | 1/1993 | Vignaud et al. |
| 5,380,325 | A | * | 1/1995 | Lahille et al. .................. 606/250 |

(Continued)

FOREIGN PATENT DOCUMENTS

| CN | 1130346 A | 9/1996 |
| DE | 4239715 | 6/1994 |

(Continued)

OTHER PUBLICATIONS

International Preliminary Report on Patentability for International Application No. PCT/EP2004/001978 dated Apr. 18, 2006, 9 pp.

*Primary Examiner* — Mary Hoffman
(74) *Attorney, Agent, or Firm* — Christie, Parker & Hale, LLP (57) ABSTRACT

A dynamic anchoring device is described. An element with a shank for anchoring in a bone or a vertebra and with a head connected to the shank is provided with a receiving part for the head and with an elastomeric pressure element acting on the head. The pressure element is formed and located in such a way that, upon a movement of the element from a first angular position of the shank relative to the receiving part into a second angular position, it exerts a return force on the head. Further, a dynamic stabilization device, in particular for vertebrae, is provided. In such a stabilization device, a rod is connected two anchoring devices. At least one of the anchoring devices is constructed as dynamic anchoring element.

31 Claims, 7 Drawing Sheets

(56) References Cited

U.S. PATENT DOCUMENTS

| | | | |
|---|---|---|---|
| 5,443,527 A | 8/1995 | Wilson | |
| 5,474,555 A | 12/1995 | Puno et al. | |
| 5,562,737 A | 10/1996 | Graf | |
| 5,672,175 A | 9/1997 | Martin | |
| 5,716,356 A | 2/1998 | Biedermann et al. | |
| 5,735,850 A | 4/1998 | Baumgartner et al. | |
| 5,797,911 A * | 8/1998 | Sherman et al. | 606/270 |
| 5,879,350 A * | 3/1999 | Sherman et al. | 606/270 |
| 5,961,356 A | 10/1999 | Fekete | |
| 5,961,517 A * | 10/1999 | Biedermann et al. | 606/86 A |
| 6,022,350 A * | 2/2000 | Ganem | 606/272 |
| 6,113,601 A * | 9/2000 | Tatar | 606/266 |
| 6,355,040 B1 | 3/2002 | Richelsoph et al. | |
| 6,623,485 B2 | 9/2003 | Doubler et al. | |
| 6,716,214 B1 | 4/2004 | Jackson | |
| 6,887,242 B2 | 5/2005 | Doubler et al. | |
| 6,896,677 B1 * | 5/2005 | Lin | 606/266 |
| 7,306,606 B2 * | 12/2007 | Sasing | 606/279 |
| 2001/0034521 A1 | 10/2001 | Bailey et al. | |
| 2002/0198527 A1 | 12/2002 | Muckter | |
| 2003/0040810 A1 | 2/2003 | Molino et al. | |
| 2003/0109880 A1 | 6/2003 | Shirado et al. | |
| 2004/0006342 A1 | 1/2004 | Altarac et al. | |
| 2004/0102781 A1 | 5/2004 | Jeon | |
| 2004/0225289 A1 * | 11/2004 | Biedermann et al. | 606/61 |
| 2005/0131410 A1 * | 6/2005 | Lin | 606/61 |
| 2005/0143737 A1 * | 6/2005 | Pafford et al. | 606/61 |
| 2005/0216003 A1 * | 9/2005 | Biedermann et al. | 606/61 |
| 2006/0095038 A1 * | 5/2006 | Jackson | 606/61 |
| 2008/0312693 A1 * | 12/2008 | Trautwein et al. | 606/246 |

FOREIGN PATENT DOCUMENTS

| | | |
|---|---|---|
| DE | 42 39 715 C2 | 4/1996 |
| EP | 0669109 | 8/1995 |
| EP | 0 669 109 B1 | 5/1999 |
| EP | 1273269 A2 | 1/2003 |
| JP | 2000-511453 | 9/2000 |
| JP | 2003-508109 | 3/2003 |
| WO | WO 98/34554 | 8/1998 |
| WO | WO 01/15612 (A1) | 3/2001 |

* cited by examiner

DYNAMIC ANCHORING DEVICE AND DYNAMIC STABILIZATION DEVICE FOR VERTEBRAE

FIELD OF THE INVENTION

The invention relates to a dynamic anchoring device and a dynamic stabilization device for bones, in particular for vertebrae, with such an anchoring device.

BACKGROUND OF THE INVENTION

Intervertebral disc defects can be treated by removal of the defective intervertebral disc by surgery and osseous fusion of the intervertebral space with the two adjacent vertebral bodies. In this method the sections of the vertebral column adjacent to the fused vertebral column segment can be overstressed, especially in the area of the intervertebral disc. Another method for treatment is to remove the defective intervertebral disc and, thereafter, to insert an artificial intervertebral disc. In the majority of cases, the rear facet joints and the ligamentous apparatus also are damaged severely. Thus, there is usually no longer any natural control of movement of the artificial intervertebral disc from the posterior side. Consequently, high shearing and rotational forces have an abrasive effect on the vertebral column segment being treated.

DE 42 39 715 C2 describes a fixation system for stabilizing vertebrae, in which rotational and alternating pressure and tension loads on the part fixed in the bone can be reduced. However, elastic damping or control of the occurring movements is not possible.

EP 0 669 109 B1 describes a device for stabilizing adjacent thoracic vertebrae allowing a damaged intervertebral disc and the intervertebral joints to be partially released from stress from the posterior side. The device comprises two pedicle screws which are rigidly connected, respectively, to a strap consisting of an elastic synthetic material and which are connected to one another via the biased strap. A pressure-resistant body slipped onto the elastic strap is further provided between the two screw heads to transmit pressure forces. The use of a textile strap of this kind with a pressure-resistant body, however, does not enable any multi-axial guidance stability of the motion segment of a vertebral column.

U.S. Pat. No. 5,474,555 describes a polyaxial bone screw with a screw element and a receiving part connected thereto for receiving a rod which allows limited motion between the receiving part and the vertebra. However, elastic damping of the motion is not possible with this screw.

U.S. Pat. No. 5,961,356 describes an anchoring element in form of a polyaxial bone screw which has a pressure element acting upon the head, wherein the pressure element comprises a spring element acting upon the inserted rod.

U.S. Pat. No. 5,562,737 discloses an extra-discal intervertebral prosthesis comprising at least a partially closed, elongated body including a compression chamber having an elastic block at one end. The block has a free face abutted by a ball joint associated with a first of two fixation means engageable in spaced vertebrae of a patient.

Thus, new anchoring devices continue to be sought which allow dynamic anchoring of a mechanical device, such as, e.g. a rod, in a bone or a vertebra and which can be used in particular for a dynamic stabilization device for stabilizing motion control and relieving the stress on an artificial intervertebral disc. In addition, it is desirable to have a dynamic stabilization device for bones, in particular for vertebrae, which allows motion control and stress relief on the human intervertebral disc from the posterior side.

SUMMARY OF THE INVENTION

The present invention provides an anchoring device comprising an element having a shank for anchoring in a bone or a vertebra and a head connected to the shank, a receiving part for receiving the head, and a pressure element acting on the head, wherein the pressure element is resilient so that upon a movement of the element from a first angular position of the shank relative to said receiving part into a second angular position the pressure element exerts a return force onto the head to urge the element towards the first angular position.

Preferred embodiments of a bone anchoring element in accordance with the invention have one or more of the following features:

the pressure element acts on the side of the head facing away from the shank;

the pressure element is formed of an elastomer;

the pressure element comprises at least one spring element;

the head comprises a flat surface on the side facing away from the shank and the pressure element comprises a flat surface cooperating therewith;

the head comprises a spherical segment-shaped section adjacent to the shank and a collar on the side facing away from the shank;

the receiving part comprises a support surface to support the head, the support surface and/or the head being polished or coated to reduce friction;

a rigid element acting on the pressure element on a side of the pressure element opposite to the head is provided;

the head and the shank are separate parts;

the head has a central axis and the shank is connectable to the head at a predetermined angle α to the central axis;

the pressure element is substantially cylindrical and comprises a first section which is resilient and a second section which is rigid and which is located on a side opposite to the head;

the second section comprises a U-shaped recess to receive a rod to be received in the receiving part, the recess forming two free legs and wherein a depth of the recess is greater than the diameter of the rod;

the first section and the second section are separate parts;

the pressure element is formed by an insert made of an elastomer and having a support surface for the head to rest against;

a second elastic pressure element is provided encompassing the head in a ring shape;

the second pressure element is shaped as O-ring or as a molded ring;

the receiving part comprises a U-shaped recess for inserting a rod and the pressure element is arranged between the head and the rod when the rod is inserted into the receiving part;

the pressure element is pre-compressed by the rod when the rod lies on the bottom of the U-shaped recess; and/or the pressure element is arranged in the receiving part under pre-stress.

The invention also provides a dynamic stabilization device for bones, in particular for vertebrae, having at least two anchoring devices connected to a rod, wherein one of the anchoring devices is formed as the anchoring device described above.

Additionally, the invention provides a method for using the dynamic anchoring device and a method for stabilizing bones, in particular for stabilizing vertebrae, wherein the anchoring device is formed as the anchoring device described above.

Further features of the invention emerge from the description of embodiments using the figures.

DETAILED DESCRIPTION OF THE INVENTION

Figure 1:
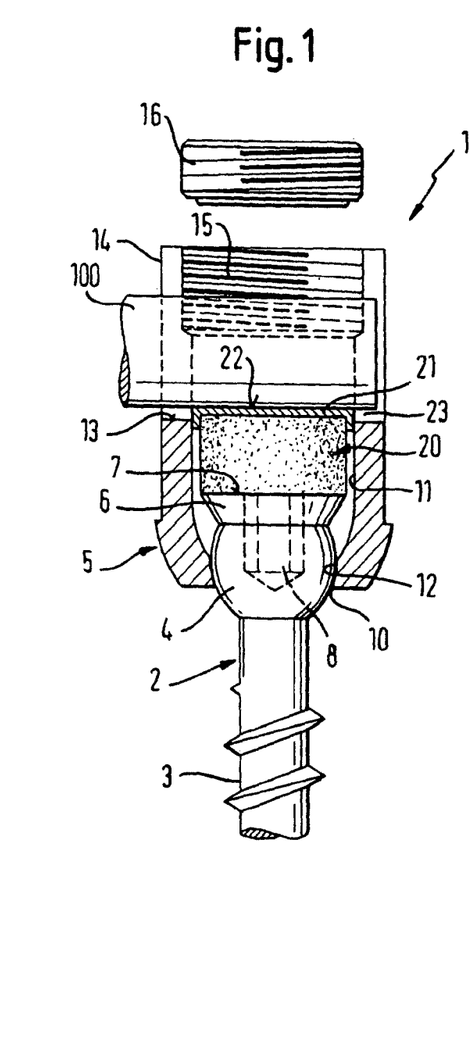
FIG. 1 shows an illustration in partial section of a first embodiment of the anchoring device in the unloaded state.
Figure 2:
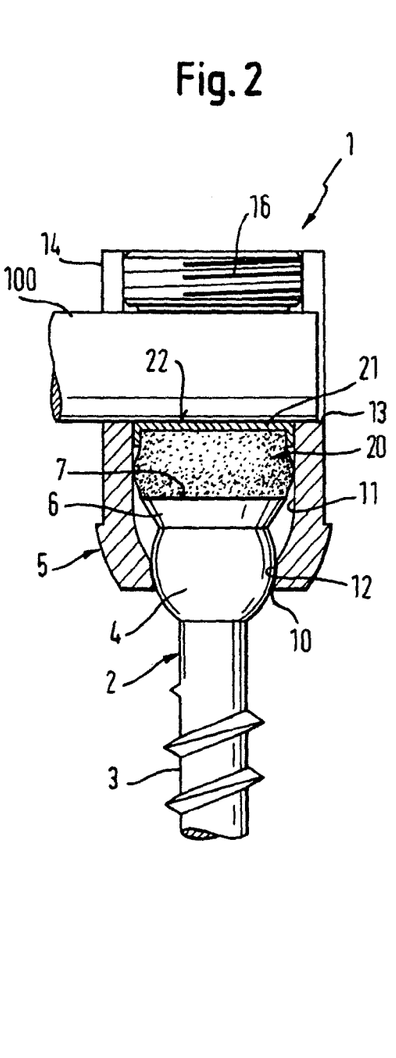
FIG. 2 shows an illustration in partial section of the anchoring device according to FIG. 1 in the loaded state in the resting position.
Figure 3:
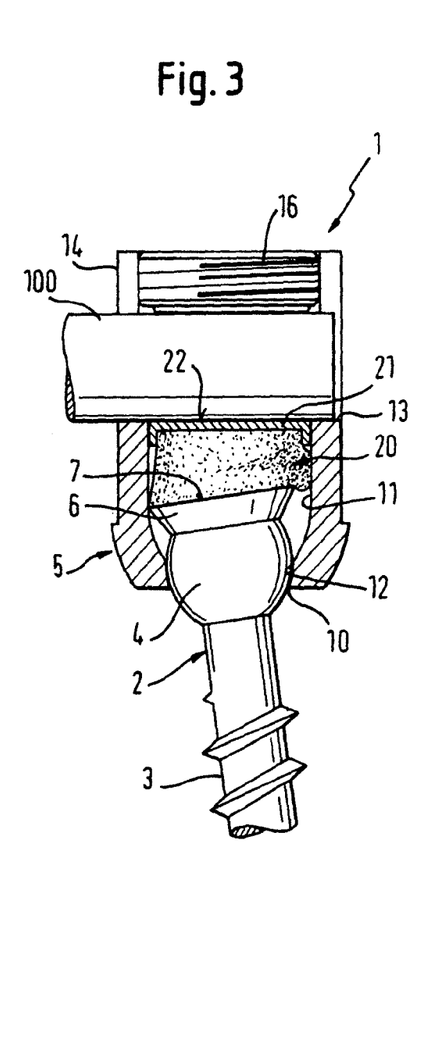
FIG. 3 shows an illustration in partial section of the anchoring device of FIG. 1 in the loaded state during the action of a force upon the anchoring element.

As can be seen in particular from FIGS. 1 to 3, in accord with one embodiment of the invention, the dynamic anchoring element 1 is formed as a polyaxial screw. It comprises a screw element 2 with a threaded shank part 3 and a head 4 formed in one piece therewith and a receiving part 5. The head 4 is substantially formed in the shape of a segment of a sphere and has on its end opposite to the shank part 3 a widened edge or collar 6, so that a flat front face 7 is formed which has a diameter which is larger than the diameter of the spherical segment-shaped section of the head. A recess for bringing into engagement with a screwing-in tool is further formed in the front face 7.

The receiving part 5 is substantially formed cylindrically symmetric and has on one of its ends a coaxial first bore 10 the diameter of which is larger than that of the threaded section of the shank 3 and smaller than the spherical diameter of the spherical segment-shaped section of the head 4. It further has a coaxial second bore 11 which is open at the end opposite the first bore 10 and the diameter of which is large enough for the screw element 2 to be inserted through the open end with its threaded section through the first bore 10 and with the spherical segment-shaped section of the head 4 to the bottom of the second bore. In the receiving part, adjacent to the first bore 10 a section 12 is provided, shaped like a segment of a hollow sphere, the radius of which is substantially identical to the radius of the section of the spherical segment-shaped head 4. The receiving part further has a U-shaped recess 13, extending from the open end towards the first bore 10, the bottom of which is directed towards the first bore 10 and by which two open legs 14 are formed, only one of which is illustrated in the figures. An inner thread 15 is formed in the receiving part adjacent to the open end of the legs 14. The width of the U-shaped recess 13 is minimally larger than the diameter of a rod 100 to be received therein which connects several such polyaxial screws. The depth of the U-shaped recess is dimensioned in such a way that when the rod is inserted a fixing screw 16 can be screwed in between the legs.

The section 12 of the receiving part which is shaped like a segment of a hollow sphere is preferably polished smooth or coated with a material which increases the sliding capacity, so the head 4 can easily be swiveled in the section 12 of the receiving part. Alternatively, or additionally the head 4 is polished smooth or coated.

Between the inserted rod 100 and the head 4 of the screw element a pressure element 20 is provided. The pressure element 20 is formed in the shape of a cylinder and has a diameter which is smaller than the inner diameter of the second bore 11 of the receiving part and which is preferably identical to the diameter of the front face 7 of the head. The axial length of the pressure element 20 is slightly larger than or identical to the distance between the front face 7 of the head 4 and the bottom of the U-shaped recess 13 in the inserted state. The pressure element is resilient, in the illustrated embodiment it is formed from an elastomer, e.g., from polyurethanes or polysiloxanes. However, any suitable biocompatible material can be used.

Between the pressure element 20 and the inserted rod 100 a cap 21 is provided, which covers the pressure element on the side facing the rod and which is constructed from an inflexible material, for example a synthetic material or a body-compatible metal. The outer diameter of the cap 21 is dimensioned in such a way that the cap is displaceable by sliding in the second bore of the receiving part and the inner diameter of the cap substantially corresponds to the outer diameter of the pressure element 20 when this is in an unloaded state. The cap overlaps the pressure element to such an extent that the pressure element is able to expand in the radial direction when put under load.

FIG. 1 shows the unloaded state in which the screw element 2, the pressure element 20 and the cap 21 are inserted into the receiving part and the rod 100 is placed into the U-shaped recess 13, but the inner screw has not yet been screwed down. In this state the side 22 of the cap 21 facing away from the pressure element 13 is at a slightly higher position than the bottom of the U-shaped recess 13, so that the rod rests with its lower side on the surface 22 of the cap and thus a gap 23 is formed between the lower side of the rod and the bottom of the U-shaped recess 13.

In operation, as shown in FIG. 1, first the screw element 2 is inserted into the receiving part 5 from the open end thereof until the head rests against the section 12 of the receiving part shaped like a segment of a hollow sphere. The screw element is then screwed into the vertebra. Then, the pressure element 20 together with the cap 21 placed thereon is inserted into the receiving part, the receiving part is aligned and the rod inserted. Finally, the inner screw 16 is screwed into the receiving part.

As illustrated in FIG. 2, the inner screw is screwed in until it presses the rod against the bottom of the U-shaped recess and thus fixes the rod. At the same time, the rod presses on the cap 21, which serves for even distribution of the force of pressure exerted by the rod on to the entire surface of the pressure element. Due to the elasticity of the pressure element it is pre-compressed via the force exerted by the rod. At the same time, the pressure element takes on a shape curved outwards in the radial direction, shown in FIG. 2. In the state shown in FIG. 2 the pressure element 20 is under bias in respect of the screw head 4 and due to the return force it presses with its lower side evenly on the front face 7 of the head. In this way, the head is pressed against the section 12 of the receiving part.

The screw element 2 screwed into the vertebral body is moved out of its resting position by a self-movement of the vertebral column. When the vertebra moves towards the rod at an angle of 90° to the rod axis there is uniform compression of the pressure element and the angle of the shank relative to the receiving part does not change. When the vertebra moves at an angle other than 90° to the rod axis, as shown in FIG. 3, there is a swiveling of the head, which easily slides in the section 12 of the receiving part. Thereby, the front face 7 of the screw head exerts a compression force on to the pressure element on one side which compresses it on one side near the edge. On the other hand, on the opposite side, the pressure element standing under pre-stress expands owing to the relief of pressure. Thus, the pressure element always remains in contact with the screw head.

Due to the elasticity of the pressure element, the compression effects a return force onto the screw head. In this way, a movement of the vertebra back into its original position in which it has been placed by the surgeon is supported.

By the choice of an elastomer material for the pressure element with a desired compressibility a limitation of motion of the vertebra can be adjusted. If the material is only slightly compressible, the device allows only a small deflection out of the resting position. If the material properties are changed, larger swivel ranges are possible. Those skilled in the art can readily substitute materials using routine experimentation. Body-compatible elastomer can be used as elastomer material, e.g., polyurethanes or polysiloxanes.

The swivel range can also or additionally be set by the selection of the diameter of the collar 6 of the screw head relative to the diameter of the second bore 11 of the receiving part. When the collar 6 abuts on the wall of the receiving part in the swiveled position of the screw element 2, no further swiveling is possible.

Figure 4:
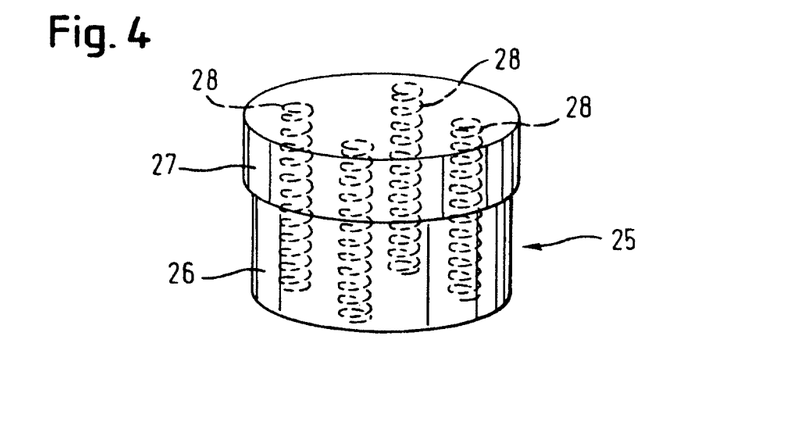
FIG. 4 shows a schematic illustration of a second embodiment of the pressure element of the embodiment of the anchoring element shown in FIGS. 1 to 3.

FIG. 4 shows a pressure element 25 according to a second embodiment. The pressure element 25 has a housing formed in a box shape, consisting of a lower part 26 and an upper part 27, which closes the lower part like a lid. Inside, at least two preferably four or more helical springs 28 are arranged opposite one another which are distanced evenly apart in the circumferential direction, and which are connected with one of their ends to the lower part and with their other end to the upper part. The helical springs 28 are arranged near the housing wall, as the compression forces are greater at the edge of the pressure element than in the center, as can be seen in FIG. 3. The strength of the helical springs is selected in such a way that a desired or required compression via the screw head can be achieved.

If the anchoring device comprises the pressure element according to the second embodiment, the cap 21 described in the first embodiment is not necessary, as the upper side of the pressure element consists of an inflexible material.

The operation of the anchoring device is like that of the first embodiment. In order to prevent lateral displacement of the pressure element 25 in the receiving part, the diameter of the pressure element is in a further modification only slightly smaller than the diameter of the second bore 11 of the receiving part.

In a further embodiment, the pressure element itself is formed as a helical spring. The diameter of the helical spring then corresponds to the diameter of the box-shaped housing according to the second embodiment. Other types of springs are also possible, e.g., one or more spring washers.

In an alternative embodiment in the elastomeric pressure element, helical springs are contained in an arrangement identical to or similar to that according to FIG. 4 and are cast into an elastomeric material during manufacture of the pressure element. These springs then serve to support the elastic properties of the elastomer.

In a modification of the first embodiment, the pressure element 20 and the cap 21 are pre-mounted in the receiving part 5 and secured against falling out, e.g., by crimped bores provided in the receiving part and countersunk bores in the pressure element corresponding therewith. In this case the pressure element 20 and the cap 21 have a coaxial central bore which enables a screw tool to be guided through to screw the screw element 2 into the bone. The bore can also be provided if the pressure element and the cap are not pre-mounted.

In a further embodiment, the pressure element is formed in such a way that the face facing the cap 21 and/or the front face 7 of the head is curved concavely towards the inside of the pressure element. This, in cooperation with the flat face of the cap and/or the screw head, creates an increase in the pressure elasticity at the edge.

Figure 6:
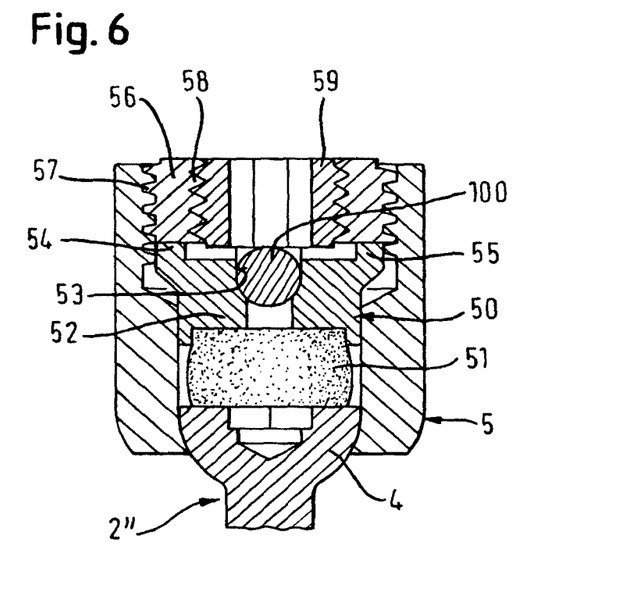
FIG. 6 shows a sectional illustration of a third embodiment of the anchoring element.

In a further modification, the head does not have the collar, but is formed, e.g., in the shape of a semi-sphere, as illustrated in FIG. 6, so that the front face has the largest diameter of the screw head. It is decisive that there is a sufficiently large front face for cooperation with the pressure element which guarantees force transmission at the edge.

Figure 5A:
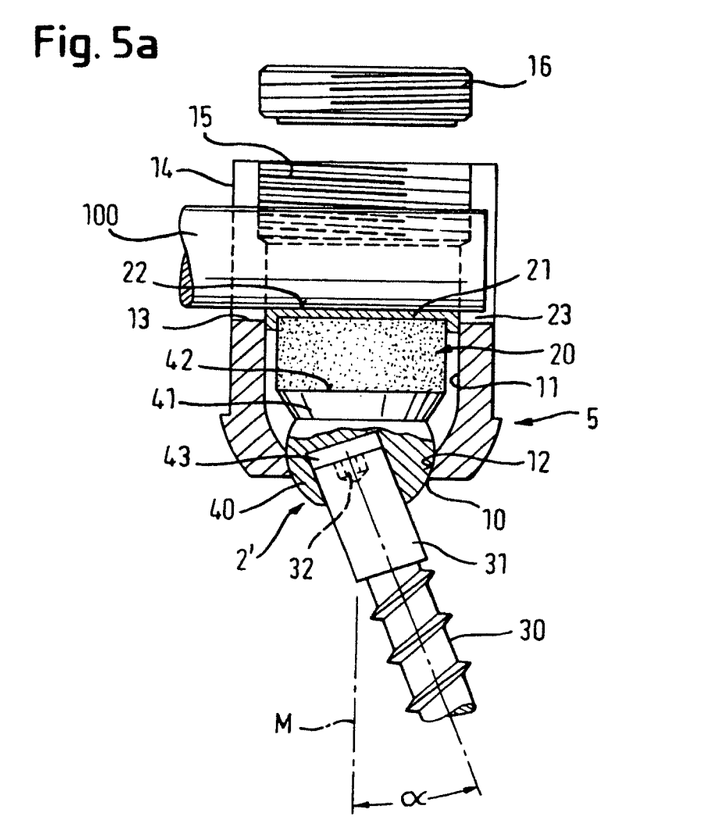
FIG. 5a shows an illustration in partial section of a second embodiment of the anchoring element.

In a second embodiment of the anchoring device shown in FIG. 5a, the resting position of the screw element 2 relative to the receiving part 5 is at an angle $\alpha$ to the central axis M of the receiving part which is different from 0°. In this case, the screw element 2' is constructed in two parts. It comprises a head 40 and a threaded shank 30 which can be connected thereto. The threaded shank 30 has on one of its ends a thread-free section 31. On this end there is further provided on the front a recess 32 for bringing into engagement with a screw tool. The head 40, like that of the screw element of the first embodiment, comprises a spherical segment-shaped section and a collar 41 adjoining the spherical segment-shaped section on the side facing away from the shank and having a front face 42 for cooperating with the pressure element. On the side facing away from the front face the head 40 has a bore 43 extending at a predetermined angle $\alpha$ to the axis of symmetry of the head. The diameter of the bore is identical to the outer diameter of the thread-free section 31 of the shank 30, so that the shank can be inserted into the bore by friction locking. To improve the clamping effect on to the inserted shank the head can have slits, not illustrated, in its wall, so that the bore has a resilient edge.

Alternatively, an inner thread is provided in the bore 43 and an outer thread on the shank section 31 matching the inner thread to allow screwing in of the shank into the head.

The remaining parts of the anchoring device are as in the embodiment according to FIGS. 1 to 3 or its modifications.

In operation first the shank 30 is screwed into the vertebra. Then, the receiving part 5 with its first bore 10 is placed diagonally onto the shank 30 or onto the projecting thread-free section 31 and then the head 40 with the pressure element and, if applicable, the cap are inserted into the receiving part in the pre-compressed state with a suitable tool and with the bore 43 slid onto the shank. The longitudinal axis of the shank 30, thus, has a predetermined angle α to the central axis of the head 40 and therefore to the central axis of the receiving part 5. Subsequently, the rod is inserted and finally the whole arrangement is fixed via the inner screw 16, as in the first embodiment. Like in the first embodiment, when the vertebra moves, the return force causes the head to be forced back into its resting position. Although the angle is preset by the angle of the bore 43, the surgeon can still perform an adjustment by rotating the receiving part about its axis or by a minimal swiveling of the head.

Figure 5B:
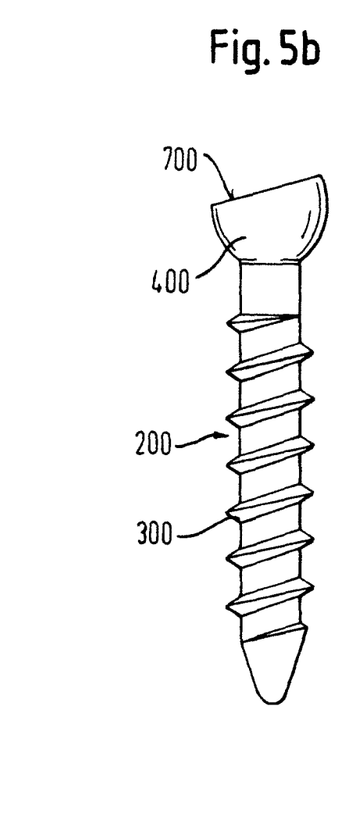
FIGS. 5b-5e show manufacturing steps for manufacturing the screw element of a modification of the second embodiment.
Figure 5C:
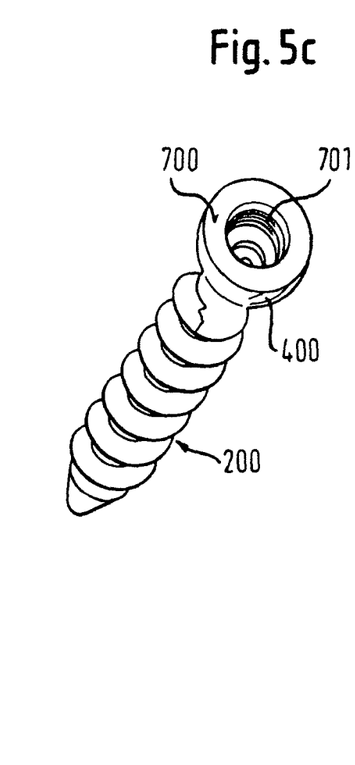
Figure 5D:
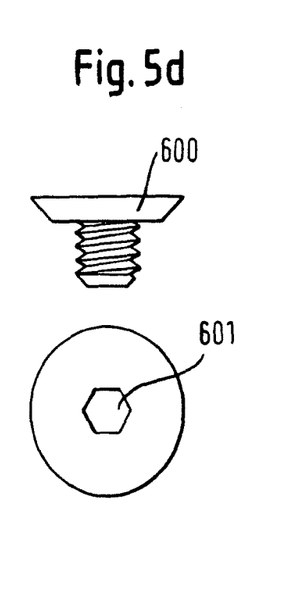
Figure 5E:
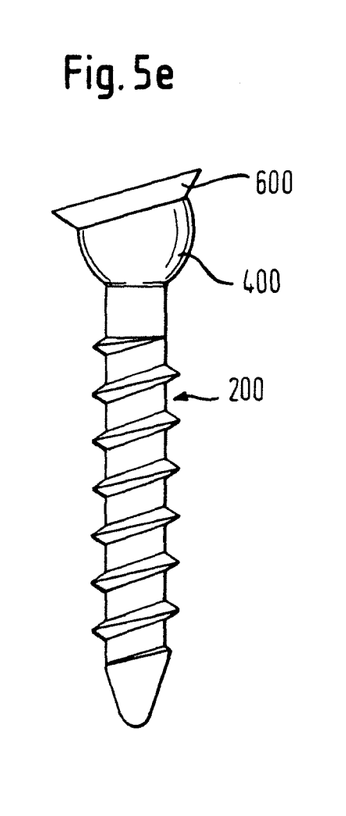

In a further modification of the second embodiment, the head is constructed in one piece with the shank, but the front face of the head which forms the support face for the elastic pressure element is at an angle to the axis of the shank. In FIGS. 5b to 5e, the manufacturing steps of a screw element 200 of this kind are shown. The screw element 200 has a threaded shank 300 and a spherical segment-shaped head 400 connected thereto in one piece. As shown in FIG. 5b, the head is milled off in such a way that the front face 700 has a predetermined angle to the axis of the shank. Subsequently, as shown in FIG. 5c, a bore 701 with an inner thread is produced, which extends perpendicular to the front face 700. Into this bore, as shown in FIG. 5c, a screw 600 with a collar-shaped head and with a recess 601 for subsequent screwing into the bone is screwed into the head, the diameter of the collar being larger than the diameter of the head 400. The finished screw element 200, shown in FIG. 5e, is then inserted into the receiving part.

In operation, the screw element 200 is inserted into the receiving part and then screwed into the bone. By means of the face 700 extending at the predetermined angle to the axis of the shank the screw element 200 has the predetermined angle relative to the receiving part in the resting position. The insertion of the pressure element and the rod takes place as previously described.

The collar can also be constructed in one piece with the screw element.

Figure 10A:
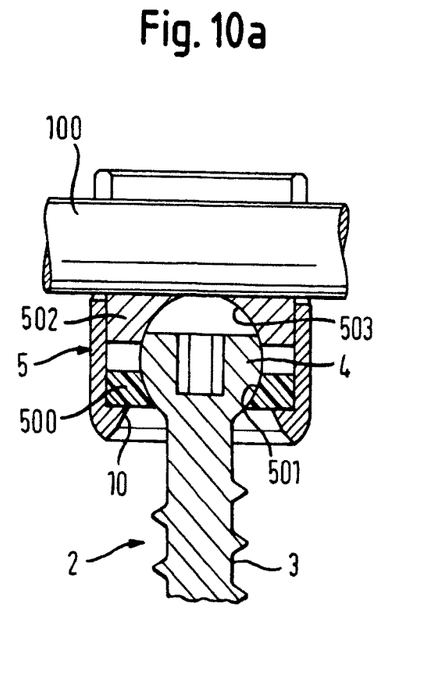
FIGS. 10a-10c show a sectional illustration of a further embodiment of the dynamic anchoring device.
Figure 10B:
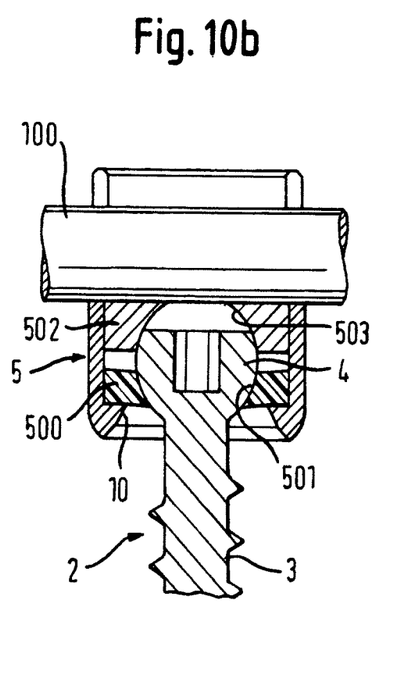
Figure 10C:
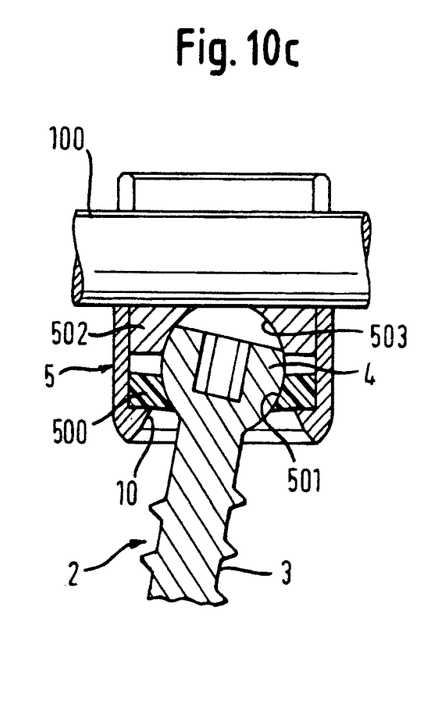

In a further modification of the second embodiment, shown in FIGS. 10a-10c, it is not the receiving part 5 itself which comprises the section shaped like a segment of a sphere against which the head rests, but in the receiving part an insert 500 made of an elastomer is provided, which is constructed with a cylindrical outer wall and surrounds the spherical segment-shaped section of the head laterally starting from the first bore 10, or which, as shown in FIG. 10a, is ring-shaped and has only a support face 501 for the screw head. Further, a rigid pressure element 502 which presses on the head 4 is provided. The pressure element 501 has a spherical segment-shaped recess which fits into the screw head. In operation, after adjustment of the screw 2 and the receiving part 5 in respect of one another, the screw head 4 is pressed via the fixing screw 16 and the pressure element 502 at a desired angle against the insert, which therein, because it is slightly compressed, is under bias, as shown in FIG. 10b. This position forms the resting position. When there is a movement of the vertebra, the screw head presses against the insert 500, so that it deforms at this point and enables the screw to move out from the resting position, as shown in FIG. 10c. Simultaneously, the increasing return force forces the head back into its resting position. In this embodiment, the desired angle of the screw shank to the receiving part, which is supposed to form the resting position, can be freely adjusted.

In a further modification, the pressure element is formed so as to be wedge-shaped.

In a third embodiment, shown in FIG. 6, the anchoring device is formed in such a way that the head and the rod can be independently loaded. For this purpose, in contrast to the first embodiment, the pressure element 50 has a first elastic section 51 and a second inflexible section 52 adjacent thereto, which are rigidly connected to one another. The inflexible section 52 has a U-shaped recess 53, the dimensions of which are such that the rod 100 can be inserted therein. The depth of the U-shaped recess of the pressure element, seen in the direction of the cylinder axis, is greater than the diameter of the rod. The open legs 54, 55 formed by the U-shaped recess thereby project beyond the rod when it has been inserted. Further, a nut or bushing type closing element 56 is provided, which has an outer thread 57 cooperating with the inner thread of the receiving part and an inner thread 58. An inner screw 59 is provided to be screwed into the closing element 56.

In operation, when a force is exerted on the legs of the rigid pressure element part 52 and the elastic pressure element part 51 via the closing element 56, a force is applied to the screw head. The rod is fixed independently via the inner screw 59. If desired, the rod can also be movably held. In this case, the inner screw is screwed in only to such an extent that the rod can still slide in the U-shaped recess of the receiving part.

In the embodiment shown, in which sections 51 and 52 are rigidly connected to one another, the pressure element 50 is constructed in one piece. In a modification, it is constructed in two pieces and then consists of an elastic part 51 according to the embodiment according to FIG. 1 and a non-elastic part 52, which has the U-shaped recess.

Figure 7:
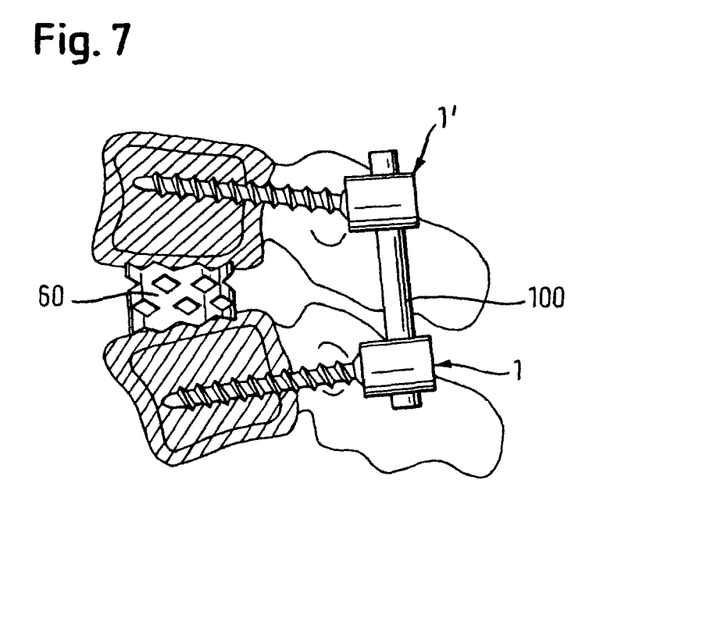
FIG. 7 shows a schematic illustration of the first embodiment of the dynamic stabilization device.

FIG. 7 shows a dynamic stabilization device for vertebrae according to a first embodiment. This is, in particular, applicable in a case in which an intervertebral disc or a vertebra is removed and replaced by a rigid fusion element 60, e.g., a tube-shaped implant with openings in the wall and, e.g., filled with bone mass to allow bones to grow in.

The stabilization device comprises two dynamic bone anchoring devices 1, 1' in the posterior area, which are connected to one another via a rigid rod 100. Each of the bone anchoring devices 1, 1' is formed according to one of the previously described embodiments. Because of the elastic construction of the pressure element and the associated damping effect there is intermittent, limited load onto the fusion element 60, resulting in acceleration of the growing in of bone in and around the fusion element. This accelerates the healing process.

Figure 8:
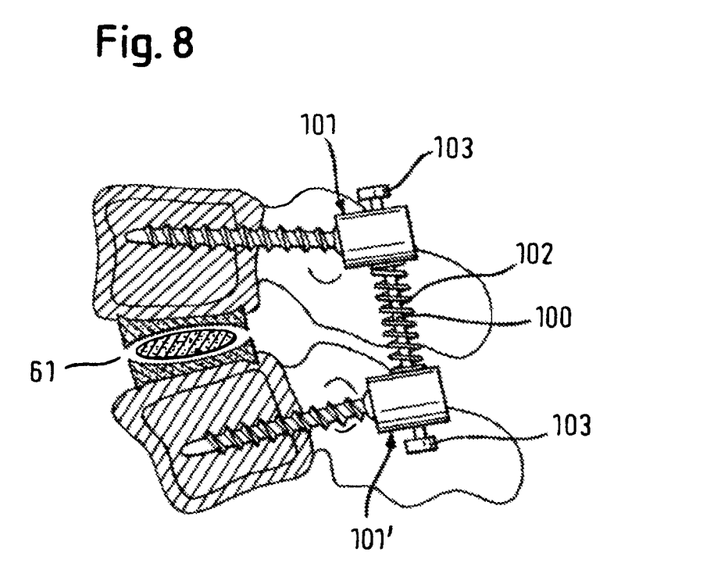
FIG. 8 shows a schematic illustration of a second embodiment of the dynamic stabilization device in a first example of application.

FIG. 8 shows a dynamic stabilization device for vertebrae according to a second embodiment. This can be applied in particular in a case in which an intervertebral disc has been removed and replaced by an intervertebral disc prosthesis 61. The stabilization device comprises two dynamic anchoring devices 101, 101' which are connected to one another via a rigid rod 100. At least one of the anchoring devices 101, 101' is formed according to the embodiment shown in FIG. 6, which is characterized in that pressure is exerted on the screw head via the pressure element 50, but the rod still remains displaceable in the axial direction. The stabilization device further comprises a spring element 102 provided on the rod between the two anchoring devices, and also at least one stop 103 on the rod arranged on the side opposite to that spring element 102 of the anchoring device in which the rod 100 is held slidingly. In the example shown in FIG. 8, two such stops are provided and the rod is slidingly held in both anchoring devices 101, 101'. The spring element 102 is inserted in between the anchoring devices under bias and thus acts as extension spring.

In operation, the combination of posterior longitudinal resiliency of the rod 100 and the polyaxial damping of the anchoring devices 101, 101' enables control of movement and relieving of the stress on the intervertebral disc prosthesis. The stabilization device can be applied for any artificial intervertebral disc structure.

Figure 9:
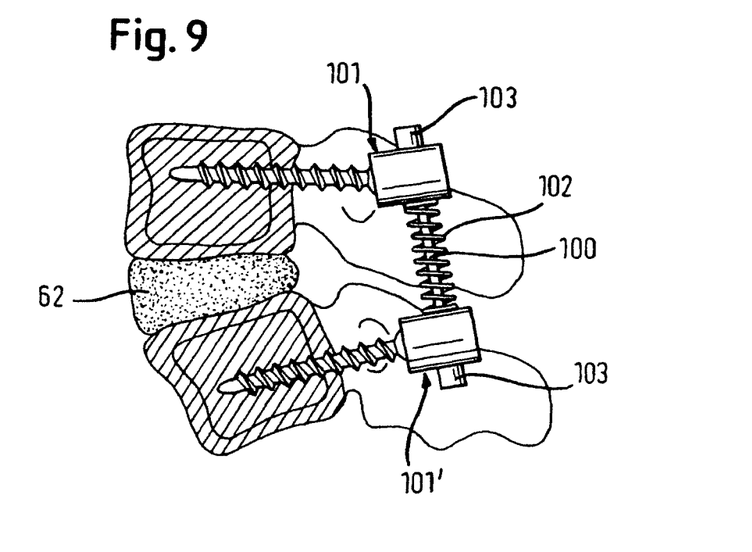
FIG. 9 shows a schematic illustration of the second embodiment of the dynamic stabilization device in a second example of application.

FIG. 9 shows a further application of the stabilization device illustrated in FIG. 8, which comprises the extension spring rod and the dynamic anchoring devices in the form of the previously described polyaxial damping screws in the posterior area. In this case of application, the human intervertebral disc is damaged to an extent that, when relieved from stress, it will recover. The stabilization device therein relieves the stress on the human intervertebral disc and, at the same time, limits the extent of movement, so that extreme movements, which would further damage the intervertebral disc, cannot occur and the intervertebral disc is able to recover in the resting phase, e.g., at night or while lying down.

Figure 11:
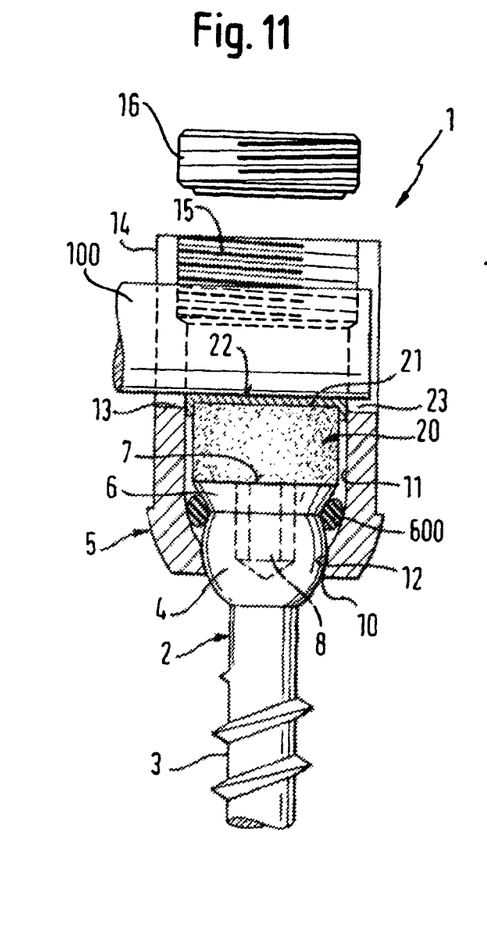
FIG. 11 shows a sectional illustration of a further embodiment of the dynamic anchoring device in the unloaded state.
Figure 12:
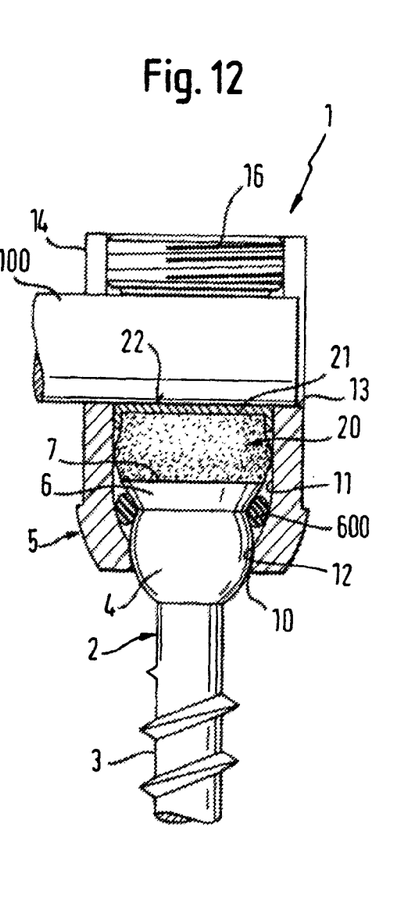
FIG. 12 shows the embodiment illustrated in FIG. 11 in the loaded state.
Figure 13:
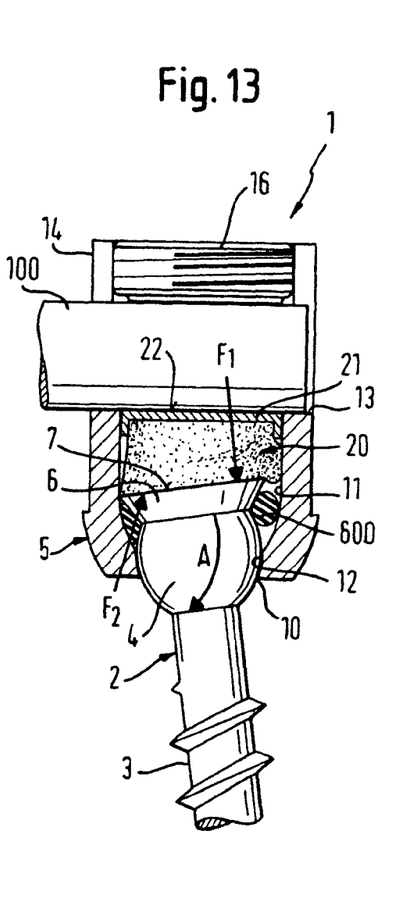
FIG. 13 shows a schematic representation of the function of the embodiment shown in FIGS. 11 and 12.

In FIGS. 11 to 13, a further embodiment of the invention is described. Elements which are corresponding to the elements of the embodiment shown in FIGS. 1 to 3 have the same reference numerals. According to FIG. 11, this embodiment comprises in addition to the elastic pressure member 20, which is arranged between the rod and the head, a second elastic pressure member 600. The second pressure member 600 is ring-shaped and arranged such that it encompasses the screw head at the location where the collar 6 is formed adjacent to the spherical segment-shaped section. In the embodiment shown, the second pressure member 600 is formed as O-ring. The outer diameter of the pressure member and its inner ring diameter are dimensioned such that in the unloaded state shown in FIG. 11 in which the pressure member is inserted into the receiver member 5, the ring is in contact with the outer side of the head and the inner wall of the receiver member. Suitably, at the time of inserting of the screw element into the receiver member the second pressure member 600 is already placed on the screw head.

In operation, in the loaded state shown in FIG. 12 in which the rod is fixed, the pressure member 600 is deformed. Due to the compression occurring when the pressure element is deformed, the pressure element is spring-biased towards the screw head. According to FIG. 13, the first pressure member 20 causes a return force acting upon the front face 7 of the screw head from the top, which is represented by the arrow $F_1$, when the screw element 2 moves out of its resting position, whereas the second pressure member 600 generates a return force, illustrated by arrow $F_2$, on the screw head acting from laterally below the front face 7 and being diagonally offset with respect to the force $F_1$. Therefore, return forces acting upon the screw head which return the latter into its original position as shown by the arrow A in FIG. 13 are increased by means of the second pressure member 600. In addition, the second pressure member 600 reduces wear of the first pressure member 20.

By selection of the materials of the first pressure member 20 and the second pressure member 600, which can be different, a desired adjustment of the damping can be achieved. For instance, the first pressure member is formed of a harder or less compressible material than the second pressure member.

In a modification of this embodiment, the second pressure element is not formed as O-ring but as a molded ring.

The invention is not limited to the above-described embodiments. Combinations of elements of the individual embodiments with elements of other embodiments are possible. In particular, the invention is also not confined to a polyaxial screw. For example, a hook can also be provided as anchoring element instead of the threaded shank. The receiving part can also be constructed in such a way that the screw can be inserted from below into the receiving part. In this case, a molded ring is provided as end stop for the screw head.

The section 12 of the receiving part which supports the head is not restricted to have a spherical shape, it can also be conical or can have another shape suitable for the particular application.

In a stabilization device using the anchoring device according to the embodiments described above, a force acting on the rod due to a movement of the bone segment or the vertebra in which the anchoring device is anchored is prevented from being fully transmitted to the area where the shank is anchored. Thus, loosening of the shank in the bone can be reduced or prevented.

Those persons skilled in the art easily recognize that the invention is not limited to a dynamic anchoring device wherein the screw element is inserted from above in the receiving part, but is also applicable to a dynamic anchoring device wherein the screw element can be inserted from below through the bore.

What is claimed is:

1. A dynamic anchoring device comprising:
    an anchoring element having a shank for anchoring in a bone or a vertebra and a head connected to the shank;
    a rod,
    a receiving part defining a bore for receiving the head, the receiving part comprising a shaped recess for inserting the rod;
    a fixation screw for fixing the rod in the recess; and
    a pressure element located inside the bore and acting on the head, the pressure element comprising a resilient portion having a first side and a second side;
    wherein when the rod is fixed in the recess by the fixation screw, the anchoring element is movable from a first angular position to a second angular position different from the first angular position, the movement exerting a compression force on the first side of the resilient portion and releasing pressure on the second side of the resilient portion, wherein the first side of the resilient portion exerts a return force onto the head in response to the compression force urging the anchoring element towards the first angular position;
    wherein a contact position of the anchoring element relative to the resilient portion is substantially constant during movement of the anchoring element from the first angular position to the second angular position.

2. The dynamic anchoring device according to claim 1, wherein the pressure element acts on a side of the head facing away from the shank.

3. The dynamic anchoring device according to claim 1, wherein the resilient portion of the pressure element is formed of an elastomer.

4. The dynamic anchoring device according to claim 1, wherein the pressure element comprises at least one spring element.

5. The dynamic anchoring device according to claim 1, wherein the head comprises a flat surface on a side facing away from the shank and the pressure element comprises a flat surface cooperating therewith.

6. The dynamic anchoring device according to claim 1, wherein the head comprises a spherical segment-shaped section connected to the shank and a collar on a side of the spherical segment-shaped section opposite to the shank, wherein the collar increases in diameter relative to the spherical segment-shaped section in a direction away from the shank, the collar defining a flat surface facing away from the shank and having a larger diameter than the spherical segment-shaped section, and wherein the resilient portion of the pressure element comprises a flat surface cooperating with the flat surface of the collar.

7. The dynamic anchoring device according to claim 1, wherein the receiving part comprises a support surface to support the head, any one of the support surface and the head being polished or coated to reduce friction.

8. A dynamic anchoring device comprising:
an anchoring element having a shank for anchoring in a bone or a vertebra and a head connected to the shank;
a rod,
a receiving part defining a bore for receiving the head, the receiving part comprising a U-shaped recess for inserting the rod;
a fixation screw for fixing the rod in the recess;
a pressure element located inside the bore and acting on the head, the pressure element comprising a resilient portion having a first side and a second side; and
a rigid element contacting the pressure element on a side of the pressure element opposite to the head;
wherein when the rod is fixed in the recess by the fixation screw, the anchoring element is movable from a first angular position to a second angular position different from the first angular position, the movement exerting a compression force on the first side of the resilient portion and releasing pressure on the second side of the resilient portion, wherein the first side of the resilient portion exerts a return force onto the head in response to the compression force urging the anchoring element towards the first angular position.

9. The dynamic anchoring device according to claim 1, wherein the head and the shank are separate parts.

10. The dynamic anchoring device according to claim 9, wherein the head has a central axis and the shank is connectable to the head at a predetermined angle α to the central axis.

11. The dynamic anchoring element according to claim 1, wherein the pressure element is substantially cylindrical and comprises a rigid portion located on a side opposite to the head.

12. The dynamic anchoring device according to claim 11, the recess of the receiving part forming two free legs and wherein a depth of the recess is greater than the diameter of the rod.

13. The dynamic anchoring device according to claim 11, wherein the resilient portion of the pressure element and the rigid portion of the pressure element are separate parts.

14. The dynamic anchoring device according to claim 1, wherein the resilient portion of the pressure element is formed by an insert made of an elastomer and having a support surface for the head to rest against.

15. The dynamic anchoring device according to claim 1, wherein a second elastic pressure element is provided encompassing the head in a ring shape.

16. The dynamic anchoring device according to claim 15, wherein the second pressure element is shaped as O-ring or as a molded ring.

17. The dynamic anchoring device according to claim 1, wherein the pressure element is arranged between the head and the rod when the rod is inserted into the receiving part.

18. The dynamic anchoring device according to claim 1, wherein the resilient portion of the pressure element is precompressed by the rod when the rod lies on the bottom of the U-shaped recess.

19. The dynamic anchoring device according to claim 1, wherein the resilient portion of the pressure element is arranged in the receiving part under bias.

20. A dynamic stabilization device for bones or vertebrae, having at least two anchoring devices connected to a rod, wherein at least one of the anchoring devices comprises:
an anchoring element having a shank for anchoring in a bone or a vertebra and a head connected to the shank;
a receiving part defining a bore for receiving the head, the receiving part comprising a U-shaped recess for inserting a rod;
a fixation screw for fixing the rod in the recess; and
a pressure element located inside the bore and acting on the head, the pressure element comprising a resilient portion having a first side and a second side;
wherein when the rod is fixed in the recess by the fixation screw, the anchoring element is movable from a first angular position to a second angular position different from the first angular position, the movement exerting a compression force on the first side of the resilient portion and releasing pressure on the second side of the resilient portion, wherein the first side of the resilient portion exerts a return force onto the head in response to the compression force urging the anchoring element towards the first angular position;
wherein a contact position of the anchoring element relative to the resilient portion is substantially constant during movement of the anchoring element from the first angular position to the second angular position.

21. The dynamic stabilization device according to claim 20, wherein a spring element is provided on the rod.

22. The dynamic stabilization device according to claim 21, wherein the spring element is arranged between the anchoring devices.

23. A method of attaching an anchoring device to a bone or vertebrae, the anchoring device comprising an anchoring element having a shank for anchoring in a bone or a vertebra and a head connected to the shank, a rod, a receiving part defining a bore for receiving the head, the receiving part comprising a U-shaped recess for inserting a rod, a fixation screw for fixing the rod in the recess, and a pressure element located inside the bore and acting on the head, the pressure element comprising a resilient portion having a first side and a second side, the method comprising:
anchoring the shank in a bone or vertebrae;
inserting the pressure element in the bore of the of the receiving part to couple the pressure element to the head; and
inserting the rod in the U-shaped recess of the receiving part to connect the receiving part to the rod;
wherein when the rod is fixed in the recess by the fixation screw, the anchoring element is movable from a first angular position to a second angular position different from the first angular position, the movement exerting a compression force on the first side of the resilient portion and releasing pressure on the second side of the resilient portion, wherein the first side of the resilient portion exerts a return force onto the head in response to the compression force urging the anchoring element towards the first angular position;
wherein a contact position of the anchoring element relative to the resilient portion is substantially constant during movement of the anchoring element from the first angular position to the second angular position.

24. A method for stabilizing bones or vertebrae with a first bone anchoring device and a second bone anchoring device, at least the first bone anchoring device comprising an anchoring element having a shank for anchoring in a bone or a vertebra and a head connected to the shank, a rod, a receiving part defining a bore for receiving the head, the receiving part comprising a U-shaped recess for inserting a rod, a fixation screw for fixing the rod in the recess, and a pressure element located inside the bore and acting on the head, the pressure element comprising a resilient portion having a first side and a second side, the method comprising the steps of:
  anchoring the first bone anchoring device in a first bone segment or a first vertebrae, the anchoring comprising:
    anchoring the shank of the first bone anchoring device in the first bone segment or first vertebrae;
    coupling the pressure element of the first bone anchoring device to the head, the resilient portion of the pressure element acting on the head;
    connecting the receiving part of the first bone anchoring device to the rod;
  anchoring the second bone anchoring device in a second bone segment or a second vertebrae; and
  connecting the second bone anchoring device to the rod;
  wherein when the rod is fixed in the recess of the receiving part of the first bone anchoring device by the fixation screw, the anchoring element of the first bone anchoring device is movable from a first angular position to a second angular position different from the first angular position, the movement exerting a compression force on the first side of the resilient portion of the first bone anchoring device and releasing pressure on the second side of the resilient portion of the first bone anchoring device, wherein the first side of the resilient portion of the first bone anchoring device exerts a return force onto the head in response to the compression force urging the anchoring element of the first bone anchoring device towards the first angular position;
  wherein a contact position of the anchoring element of the first bone anchoring device relative to the resilient portion is substantially constant during movement of the anchoring element of the first bone anchoring device from the first angular position to the second angular position.

25. The method according to claim 24, wherein the second bone anchoring device is a monoaxial or a polyaxial bone screw.

26. A dynamic anchoring device comprising:
  an anchoring element having a shank for anchoring in a bone or a vertebra and a head connected to the shank;
  a rod;
  a receiving part for receiving the head, the receiving part having a channel to receive a rod,
  a resilient pressure element acting on the head, the resilient pressure element having a first side and a second side;
  a fixation device configured to attach to the receiving part to fix the rod in the receiving part;
  wherein the pressure element is pre-stressed against the head when the rod is inserted into the receiving part and fixed by said fixation device;
  wherein when the pressure element is fixed in the receiving part by the fixation device, the first side of the pressure element exerts a restoring force onto the head, wherein the exerting of the restoring force is in response to movement of the anchoring element whereby the head is pivoted in the receiving part to exert compression force on the first side of the pressure element and release pressure on the second side of the pressure element;
  wherein when the rod is fixed by the fixation device, the fixation device is spaced from the head; and
  wherein a contact position of the head relative to the resilient pressure element is substantially constant during movement of the anchoring element.

27. A dynamic anchoring device comprising:
  an element having a shank for anchoring in a bone or a vertebra and a head connected to the shank,
  a receiving part defining a bore for receiving the head, the receiving part being connected to an external device,
  a resilient pressure element located inside the bore and acting on the head, the resilient pressure element having a first side and a second side,
  wherein when the pressure element is fixed in the receiving part and pre-stressed against the head, the first side of the pressure element exerts a restoring force onto the head in response to movement of the bone or the vertebra, the movement exerting a compression force on the first side of the pressure element and releasing pressure on the second side of the pressure element, wherein a contact position of the head relative to the resilient pressure element is substantially constant during movement of the bone or vertebra, wherein a force acting on the external device is prevented from being transmitted to the shank.

28. A dynamic anchoring device comprising
  an element having a shank for anchoring in a bone or a vertebra and a head connected to the shank,
  a receiving part for receiving the head, the receiving part having a longitudinal axis and a bore through which the shank is inserted,
  and a resilient pressure element located inside the bore along the longitudinal axis and acting on the head, the resilient pressure element having a first side and a second side,
  wherein when the pressure element is fixed in the receiving part and pre-stressed against the head, the first side of the pressure element exerts a restoring force onto the head in response to movement of the bone or the vertebra, the movement exerting a compression force on the first side of the pressure element and releasing pressure on the second side of the pressure element;
  wherein a contact position of the head relative to the resilient pressure element is substantially constant during movement of the bone or vertebra.

29. A dynamic stabilization device for bones, in particular for vertebrae, having at least two anchoring devices connected to a rod, wherein at least one of the anchoring devices comprises:
  an element having a shank for anchoring in a bone or a vertebra and a head connected to the shank, a receiving part defining a bore for receiving the head, and
  a resilient pressure element acting on the head, the resilient pressure element having a first side and a second side,
  wherein the pressure element is located inside the bore between the rod and the head when the devices are connected to the rod,
  wherein when the devices are connected to the rod, the pressure element is pre-stressed against the head, and the first side of the pressure element exerts a restoring force onto the head in response to movement of the bone or the vertebra, the movement exerting a compression force on the first side of the pressure element and releasing pressure on the second side of the pressure element,
  wherein a contact position of the head relative to the resilient pressure element is substantially constant during movement of the bone or vertebra.

30. A method for using an anchoring device for anchoring an external device in a bone, the method comprising:
  providing an anchoring device comprising:
    an element having a shank for anchoring in a bone or a vertebra and a head connected to the shank, a receiving part for receiving the head, the receiving part having a longitudinal axis and a bore hole through which the shank is inserted, and a resilient pressure element located along the longitudinal axis and acting on the head, the resilient pressure element having a first side and a second side;

anchoring the shank in the bone; and connecting the receiving part to an external device, thereby compressing the pressure element against the head, wherein when the pressure element is fixed in the receiving part and compressed against the head, the first side of the pressure element exerts a restoring force onto the head in response to movement of the bone or the vertebra, the movement exerting additional compression force on the first side of the pressure element and releasing pressure on the second side of the pressure element, wherein a contact position of the head relative to the resilient pressure element is substantially constant during movement of the bone or vertebra.

31. A method for stabilizing bones, in particular for stabilizing vertebrae, with a first bone anchoring device and a second bone anchoring device, at least the first bone anchoring device comprising an anchoring element having a shank for anchoring in a bone or a vertebra and a head connected to the shank, a rod, a receiving part defining a bore for receiving the head, the receiving part comprising a U-shaped recess for inserting a rod, a fixation screw for fixing the rod in the recess, and a pressure element located inside the bore and acting on the head, the pressure element comprising a resilient portion having a first side and a second side, the method comprising the steps of:

anchoring the shank of the first bone anchoring device in a first bone segment or a first vertebra;

anchoring the second bone anchoring device in a second bone segment or a second vertebra; and connecting the first and the second bone anchoring devices to the rod, thereby compressing the resilient pressure element;

wherein when the rod is fixed in the recess by the fixation screw, the anchoring element of the first bone anchoring device is movable from a first angular position of the first bone anchoring device to a second angular position different from the first angular position, the movement exerting a compression force on the first side of the resilient portion and releasing pressure on the second side of the resilient portion, wherein first side of the resilient portion exerts a return force onto the head in response to the compression force urging the anchoring element of the first bone anchoring device towards the first angular position;

wherein a contact position of the anchoring element relative to the resilient portion is substantially constant during movement of the anchoring element from the first angular position to the second angular position.

* * * * *

UNITED STATES PATENT AND TRADEMARK OFFICE
CERTIFICATE OF CORRECTION

| | | |
|---|---|---|
| PATENT NO. | : 8,562,652 B2 | Page 1 of 1 |
| APPLICATION NO. | : 10/841862 | |
| DATED | : October 22, 2013 | |
| INVENTOR(S) | : Lutz Biedermann et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2168 days.

Signed and Sealed this
Seventeenth Day of March, 2015

Michelle K. Lee
*Director of the United States Patent and Trademark Office*

UNITED STATES PATENT AND TRADEMARK OFFICE
CERTIFICATE OF CORRECTION

PATENT NO. : 8,562,652 B2  
APPLICATION NO. : 10/841862  
DATED : October 22, 2013  
INVENTOR(S) : Lutz Biedermann et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2225 days.

Signed and Sealed this
Sixteenth Day of June, 2015

Michelle K. Lee
*Director of the United States Patent and Trademark Office*